United States Patent [19]

Baligadoo

[11] Patent Number: 5,175,187
[45] Date of Patent: Dec. 29, 1992

[54] SYNERGISTIC COMPOSITIONS FOR THE TREATMENT OF CORONARY INSUFFICIENCY AND METHODS OF USE THEREOF

[76] Inventor: Soorianarain Baligadoo, Center of Research Medicales, SSR, University de Maurice, Moka, Mauritius

[21] Appl. No.: 401,869

[22] Filed: Mar. 6, 1989

[51] Int. Cl.⁵ .............................................. A61K 31/36
[52] U.S. Cl. ................................................... 514/464
[58] Field of Search ........................................ 514/464

[56] References Cited

PUBLICATIONS

Chem. Abstract (New) 103-64578x (1985).
Chem. Abst. vol. 106 (1987) 1131424.
Dialog. No. 5859645/85105155, M. Pfisterer, et al., Effect of short and long term administration of amidarone ischaemia-induced left ventricular dysfunction. voir resume & Drugs (Australia) 1985, 29/Suppl. 3, (23-29).
Dialog. No. 5644342/84140008, F. Follath: Medikamentenwahl und Dosierung bei Angina Pectroris, vior resume & Schweiz Med. Wochenschr (Swiz.) 1984, 114/21 suppl. 16, (65-59).
Chem Abstrs. vol. 101, 1984, G. R. Hasegawa, et al., Visual compatibility of amiodarone hydrochloride injection with other injectable drugs, p. 299, resume 235444r, Am. J. Hosp. Pharm. 1984, 41(7), 1379-80.

*Primary Examiner*—S. J. Friedman
*Attorney, Agent, or Firm*—Omri M. Behr; Matthew J. McDonald

[57] ABSTRACT

There are disclosed pharmaceutical preparations and methods for the use thereof which have a cardioprotective action useful in coronary insufficiency, in the prevention of the constitution of an infarction or of sudden death. It consists in the utilization of amiodarone, a nitrate derivative and a beta-blocker.

18 Claims, No Drawings

SYNERGISTIC COMPOSITIONS FOR THE TREATMENT OF CORONARY INSUFFICIENCY AND METHODS OF USE THEREOF

FIELD OF THE INVENTION

There are disclosed pharmaceutical preparations and methods for the use thereof which have a cardioprotective action useful in coronary insufficiency, in the prevention of the constitution of an infarction or of sudden death. These methods comprise the utilization of amiodarone, a nitrate derivative and a beta-blocker.

BACKGROUND OF THE INVENTION

In coronary insufficiency, one observes a high frequency of sudden death particularly in acute coronary insufficiency which may culminate in the occurrence of myocardial infarction. Some cases of sudden death are related to arrhythmias consecutive to coronary insufficiency itself. It would be desirable to contemporaneously decrease the consumption of oxygen, increase the myocardial irrigation and also exercise a preventive effect against arrhythmias.

It has been observed that coronary thrombosis induces a phenomenon called stunned myocardial syndrome consecutive to the prolonged ischaemia of the heart. This phenomenon prevents the obtention of optimal benefits following reperfusion.

SUMMARY OF THE INVENTION

The utilization of a nitrate compound is desirable in the first hours of an infarction. Applicant herein has demonstrated the usefulness of a nitrate derivative in the treatment of acute coronary insufficiency, infarction and in the treatment of the ischaemia present in the border zone of an infarct and in the area threatened by infarction.

This work demonstrated the existence of sub-groups of patients where the undesirable effects of the administration of a nitrate derivative were relatively important. Hence, it would be desirable to administer a composition which cancels the secondary effects, intensifies the anti-ischemic effect and allows a more prolonged anti-ischemic effect with a clinically detectible synergy.

There is provided a method of obtaining cardioprotective action for a patient suffering from coronary insufficiency and thereby reducing the probability of incidence of myocardial infarction in such a patient which comprises administering to such patient a cardioprotectively sufficient amount of protective agents comprising amiodarone in conjunction with at least one member of the group consisting of a coronary vasodilator having at least one nitro group and a beta blocker. Preferably, at least one of said vasodilators and at least one of said beta blockers is employed.

Suitably, the nitro containing dilator is selected from the group consisting of trinitrine and isosorbide dinitrate and the beta blocker is selected from the group consisting of acetbutolol, metoprolol and atenolol. The recitation of dilators or beta blockers is not intended as limiting or critical.

The protective agents are administered separately or in associated form by at least one of the routes of administration selected from the group of methods consisting essentially of oral, sublingual, intravenous, subcutaneous, and inhalation administrative routes.

Suitably, the ratio by weight of amidarone to the nitro containing coronary dilator is 100 to between 1 and 10 to between 8 and 25, with the administered dosage being between about 2 and about 30 mg per kg bodyweight per day.

In one mode, the protective agents are administered within the first 30 minutes after onset of apparent cardiac insufficiency and, suitably, the administration is repeated at least once at intervals of between 30 and 60 minutes after the first administration.

There are also provided cardioprotective agents for administration to a patient suffering from coronary insufficiency to thereby reduce the probability of incidence of myocardial infarction in such a patient which comprise a combination of cardioprotectively sufficient amounts of amiodarone and a coronary vasodilator having at least one nitro group and a pharmacologically acceptable carrier.

In such agents, the ratio by weight of amidarone to the nitro containing coronary dilator is between 10 and 40 to 1, and suitably, the nitro containing dilator is selected from the group consisting to trinitrine and isosorbide dinitrate.

The components are compounded in a form suitable for administration by the oral, sublingual, intravenous, subcutaneous, or inhalation administrative routes.

In a further embodiment the above identified agents may comprise amiodarone and a beta blocker. Suitably, the ratio by weight of amiodarone to beta blocker is 100 to between 8 and 25 and the total administered dosage is between about 2 and about 30 mg per kg bodyweight per day.

It is within the contemplation of the present invention that the compositions disclosed herein may be utilized with fibrinolytic agents such as streptokinase, urokinase, eminase, RTPA and the like.

CLINICAL STUDIES

Clinical experiments were performed to determine the efficacy of certain cardioprotective agents. In the first series of experiments studies were carried out on 50 consecutive patients with an acute myocardial infarction, to observe the effects of the administration of intravenous isosorbide dinitrate at a dose varying from 2.5 to 7.5 mg per hour. The effect of intravenous amiodarone only administered during 24 hours was also studied in 50 consecutive patients with a myocardial infarction at a dose of 10 mg/kg/24 hrs.

In a second series of experiments patients were treated with a simultaneous association of amiodarone with isosorbide dinitrate (ISDN). Both drugs were administered in combination during the early hours of an infarction in 30 patients. ISDN was first administered at a predetermined posology of 2-10 mg/hour to bring about an optimal efficacy of ISDN prior to subsequent administration of amiodarone without provoking an undesirable drop in arterial pressure.

During case by case analysis, the existence of subgroups of patients was noted in whom this association is particularly helpful as shown by the following example: in a case of impending infarction with circumferential severe ischaemia where ventricular fibrillations occurred preceded by frequent and abrupt elevations of arterial pressure, upon intravenous administration of ISDN there was a reduction of ischaemia as observed by electrocardiography (E.C.G.) and a drop in frequency of ventricular fibrillations. Addition of amiodarone brought about cessation of episodes of ventricular fibrillation and a considerable decrease of ischaemia as observed by E.C.G. The episodes of raised arterial pressure stopped and the patient survived. Under this regime, episodes of sudden deaths stopped. Evidence of efficacy was definitely observed in 4 cases where there was no accompanying arrhythmia, a most surprising finding. It was also observed that intravenous administration of amiodarone after prior administration of ISDN was associated with a further and significant decrease of ischaemia as studied by praecordial cartography as well as by clinical symptoms and signs in 21 of 30 patients. In 4 patients, a complete and unexpected disappearance of electrical signs of acute myocardial ischaemia was noted, suggesting cessation of the process leading to infarction. The effects of ISDN were observed to be a rapid onset whereas those of amiodarone-induced efficacy on ischaemia took effect clearly, only after a few hours and increased with time.

The experiments were repeated in reverse order. The administration of ISDN after preliminary intravenous administration of amiodarone brought about a most significant decrease of electrical signs in myocardial ischaemia among 6 of 10 cases studied. Electric signs of cardiac ischaemia completely disappeared 15 and 20 minutes respectively in 2 cases after the start of administration of ISDN at doses used by applicant.

In two controlled observations, resting angina appeared most frequently during the day and could be considered as Prinzmetal's angina of great severity. In these cases a perfusion of ISDN at a mean dose of 6 mg/hr prevented attacks but the pain recurred as the dose was decreased. A trial was therefore performed to administer amiodarone. It was observed that after direct injection of 100 mg of amiodarone followed by a perfusion, there was a cessation of anginal attacks at a mean dose of 2 mg/hr of ISDN. Pain recurred associated with electrical signs of ischaemia on cessation of ISDN perfusion.

This experiment clearly demonstrated synergy in 2 patients where a reduction of the necessary dose of the nitrate derivative was obtained upon combined administration with amiodarone.

A clinical study was carried out among 3 comparable groups of 48 patients, one group receiving only ISDN first intravenously and then as tablets, one group receiving amiodarone and one group receiving a combination of both drugs. Higher beneficial effects were observed with the combined drugs on several parameters including mortality, infarct size pain, ST segment elevation on E.C.G., the number of areas having a raised ST segment on "precordial cartography" and incident of left ventricular failure. These results confirmed the importance of using these two drugs in combination.

The experiments described above were repeated with intravenous amiodarone and intravenous nitroglycerin administered in the two orders in two groups of 6 patients. A synergy of this new association in reducing electrical signs of ischaemia was noted.

With the observed synergy of amiodarone with isosorbide dinitrate and of amiodarone with intravenous nitroglycerin, one may conclude that the mode of action is common to all nitrate derivatives in general. The intensity of the observed synergy at these doses is surprising and may be due to as yet unknown mechanisms at the cellular level.

The observation by the applicant of this synergy occurring clearly only with doses of amiodarone that may be considered to be high prompted further studies on synergy between amiodarone and other drugs with a view of reducing the size of the initial bolus dose. The applicant performed studies with a number of drugs including dypindamole, calcium blockers and beta blockers and noted clear synergy in bolus doses only between amiodarone and a beta-blocker. It was clearly observed in 2 cases of severe angina with repeated frequent episodes of severe angina, clinically and electrically well-defined that the episodes could be prevented by the administration of bolus doses of either ISDN 24 mg, Amiodarone 100 mg or of ISDN 24, Amiodarone 25 mg and propanolol 1 mg.

However the association of amiodarone and a beta-blocker is contra-indicated in French text books and in the French guidelines for doctors and is therefore not suggested by the state of the art previous to the present work.

In a third series of experiments, the association of amiodarone and beta-blocker was investigated. To find out whether the action of amiodarone is uniquely due to its effect on beta adrenergic receptors, and to study dose ranges at which synergy occurs and the limits of contra-indications, progressively increasing doses of amiodarone and a beta-blocker were administered to patients suffering from a stable chronic angina in the two orders: The following surprising observations were made:

When the beta-blocker was administered first, followed by amiodarone there was a statistically higher efficacy with the combination of drugs in comparison to the beta-blocker only, with no significant major undesirable effect in a group of 81 patients.

The experiment was performed as follows: A beta-blocker was administered over a period of 3 weeks followed by the administration of the beta-blocker to half of the patients and a reduced dose of beta-blocker in combination with amiodarone to the other half for a second period of 6 weeks with measurements of relevant parameters at 3 weeks interval. A superiority of the association of drugs was observed on the statistical analysis of the symptoms and of electrical parameters on exercise electrocardiography in the patients as a whole as well as on 24 hours dynamic E.C.G. monitoring in 12 patients. This suggests the presence of a pharmacological action that is clinically and statistically significant and that is distinct from an anti-adrenergic action. The beta-blocker used was atenolol in 35 cases, acebutolol in 10 cases, metoprolol in 10 cases, sotalol in 10 cases, tertatolol in 6 cases and propanolol in 10 cases.

When amiodarone was administered first followed by a beta-blocker in 30 cases, significant additional effects on heart rate, blood pressure and sometimes mild increases in auriculo-ventricular conductions were observed after administration of lesser doses than usual of the beta-blocker. These increments of observed effects occurred rapidly with the first doses of the beta-blocker. Exercise duration on bicycle tests increased sharply and significantly when exercise was limited previously by angina and ST segment change. The increase in exercise capacity was associated with a greater intensity of the detectable anti-ischemic effect of the combination. These were observed with atenolol, acebutolol and propanolol. Thus the association of amiodarone with a beta-blocker, with the advice that the patient receives the beta-blocker first and that it is checked that the patient can tolerate the beta-blocker at the cardiac level and that the auriculo-ventricular conduction is not abnormally increased, is a clinically useful observation. It thus appears that certain undesirable effects of the association of amiodarone and a beta-blocker are due to an increase of beta-blocking effects among certain patients who cannot tolerate a high beta-blocking effects. Testing with a beta-blocker when it shows no abnormal sensitivity to a beta-blocker allows the use of an association of a beta-blocker and amiodarone in the doses defined by the applicant.

The increase in conduction time when observed with the first doses of beta-blocker did not further increase with time with maintenance doses of both drugs. It is concluded that the highly beneficial effects of the proposed association are generally linked both to a mode of action specific to amiodarone and different from the beta-blocking effect and also to the obtention of a higher beta-blocking effect with a smaller than usual dose of beta-blocker. This facilitates the reduction of the dose of the beta-blocker on one hand and the reduction of the dose of amiodarone on the other hand. It also limits any secondary effects of both amiodarone and of a beta-blocker. Thus the combination of amiodarone and of a beta-blocker improves the quality of life of a patient with coronary insufficiency in comparison to the use of a beta-blocker only. Two main factors influence the global effect on the quality of life in anginal patients: exercise performance and sexual dysfunction. These two parameters are statistically much less severely affected by the combination of drugs at the doses used than with a beta-blocker alone at the standard dose ($P < 0.001$) in a Quality of Life study performed simultaneously with the clinical study described above.

The association of amiodarone and beta-blocker by IV administration was studied. These studies were designed to compare in groups of 6 patients the effects of progressively increasing bolus doses of amiodarone and of propanolol, a beta-blocker with an immediate clinical effect. These were compared with effects of a propanolol-amiodarone combination containing progressively increasing doses of propanolol.

It was found 1) that administration of small doses of propanolol (1-5 mg) very significantly increased the clinical effects of small bolus doses of amiodarone 2) that the immediate effects of a rapid injection of an association of 1 mg of propanolol and 25 mg of amiodarone exceeded the immediate effects of those of 50 mg of amiodarone and exceeded the delayed effects of 4 mg of propanolol.

Based on these experiments a preparation was developed containing 1 mg of propanolol and 25 mg of amiodarone which was found to be at least as potent as 50 mg of amiodarone on certain parameters and as potent as 3 mg of propanolol on the same parameters and associated with less side-effects than the 2 drugs used separately in clinically potent doses.

The above-referenced doses of beta-blockers that potentiate I.V. amiodarone were found in studies of 2 groups of 8 patients with unstable angina to be synergistic with amiodarone in its anti-ischemic effects producing a much earlier effect on some parameters of ischemia (myocardial oxygen consumption and ST segment change) than when amiodarone is used alone. The dose of amiodarone required to produce in two hours, a 20% decrease in ST segment elevation is markedly reduced if 1 mg. of propanolol or 2 mg. of atenolol is concurrently administered.

An IV solution containing amiodarone 50 mg., propanolol 1 mg. and ISDN 2 mg. has now been used with success in 20 patients with acute severe coronary insufficiency as a bolus does, repeated every hour for 12 hours. A similar solution containing acebutolol 5 mg. instead of propanolol has been used in 12 patients. Compared to results in comparable control patients, the results obtained with the novel combination are extremely satisfactory with a lesser incidence of myocardial infarction, of severe arrhythmias and of sudden death.

The association of amiodarone, a beta-blocker and a nitrate by IV administration was then studied.

Experiments were also performed in acute coronary insufficiency in 5 patients with acute myocardial infarction using bolus doses of a preparation containing 1 mg propanolol and 25 mg of amiodarone, compared to effects of 2 mg of isosorbide dinitrate used separately. A synergy was observed between ISDN and the combination of beta-blocker and amiodarone. In all patients studied the administration of IV ISDN (2-3 mg/hour) after the previous administration of propanolol and amiodarone brought a much greater decrease of ischaemia and in 2 cases a complete disappearance of ischaemia at the moment when the 3 drugs were used simultaneously.

In a fourth series of experiments, oral administration of the pharmaceutical preparations hereof were ivestigated in infarction and in the infarctoid syndrome.

A comparison was carried out in 8 patients suffering from an infarction and examined within 30-60 minutes after the onset of pain the effects of the administration of either:

Association A: 20 mg oral ISDN and 5 mg sub-lingual ISDN, or

Association B: consisting of the following preparations administered by oral means: (i) Amiodarone 400 milligrams, (ii) Atenolol 50 milligrams, (iii) ISDN 20 mg and (iv) ISDN 5 mg by the sub-lingual route.

More highly beneficial effects as measured by electrical indices of ischaemia and the usual indices of the consumption of oxygen were observed with Association B which did not induce any significant undesirable side effects.

The immediately foregoing experiments were repeated but substituting 100 mg acebutolol and 20 mg of propanolol respectively for 50 mg of atenolol. Once again, significantly more beneficial effects were observed with Association B than with the effects of association A as defined above and based on the same criteria.

It thus appears that the beneficial effects observed in the two clinical conditions (chronic angina and acute infarctoid syndromes) by the administration of the association of amiodarone and atenolol, of amiodarone and acebutolol, of amiodarone and propanolol demonstrate a synergy of the effects of amiodarone on one hand and the effects of the beta-blocker on the other.

The beneficial effects of the association of amiodarone with acebutolol on, of amiodarone with atenolol and of amiodarone with propanolol may be extended to the general class of beta-blockers.

In a fifth series of experiments, the effects in the maintenance therapy of chronic angina pectoris of the simultaneous association of amiodarone, a beta-blocker and a nitrate derivative in a once a day single dose were observed.

Beta-blockers, atenolol, acebutolol, metoprolol, sotalol and tertatolol were administered to each of 6 patients. In the same patients each time the effects were observed in:

1. Exercise induced angina and exercise-induced electrocardiographic changes.

2. Daily occurrence of anginal symptoms.
3. Side effects.
4. Quality of life parameters on 3 weeks intervals.

There was administered an association of a low-dose beta-blocker+amiodarone+oral nitrate+sub-lingual nitrate. The effect were compared to each drug used separately and in progressive combination starting from 1 drug to 3 drugs, the nitrate derivative being tested in its two forms oral and sub-lingual, separately and in combination.

The experiments demonstrate a clear superiority of the association of the three drugs as compared to the combination of two compounds and to one single compound. The superiority was assessed both on exercise tests and on symptoms occurrence. The association of the 3 compounds induced a significant improvement in the Quality of Life. The effects are generally present with all beta-blockers used and with the three forms of nitrates used, isosorbide dinitrate, nitroglycerin and isosorbide mononitrate.

MODES OF ADMINISTRATION AND CLINICAL USES a) Oral chronic administration:

One treatment should ideally use the 3 active substances in the novel combination in a form for oral administration in weight ratios (approximate weight) of amiodarone/ISDN/atenolol of 15:2:5 more particularly preferred in the ratio 150 mg:20 mg:50 mg.

In presence of an acute sensitivity to the effects of beta-blockers and mainly among patients where the initial heart rate is low one can envisage a lower dose of beta-blocker for example: 25 mg atenolol instead of 50 mg and with a weight ratio of amiodarone/ISDN/atenolol 15:2:2.5.

In cases of hypersensitivity to beta-blockers and/or of a contra-indication to beta-blockers the combination employed forms part of a unit dose preferentially a tablet with the active substances in the weight ratios (approximate) of amiodarone/ISDN varying from a ratio of 10:1 to 5:1, in preference 7.5:1 and particularly in the weight of 150 mg/20 mg. Glyceryl trinitrate (nitroglygerin), isosorbide mononitrate or Pentaerithrytyl tetranitrate or erithrytyl tetranitrate may be substituted for isosorbide dinitrate.

b) Oral administration-Emergency treatment

In the management of emergencies, such as a severe coronary insufficiency, the preferred combination comprises the active substances described above in one unit with however the administration of a nitrate derivative which is rapidly released or rapidly absorbed by the sub-lingual route, and in preference in the form of nitroglycerin or ISDN. This combination forms part of a unit dose but for practical reasons and development costs, two unit doses may be employed whereby one is described above for oral administration and the other by the sub-lingual, inhalation and trans-dermal routes. When hypersensitivity to beta-blockers has been observed, the preferred form would include in one unit for administration amiodarone and a nitrate derivative, preferentially amiodarone and isosorbide dinitrate (ISDN) in weight ratios (approximate to exact) varying from 20:1 to 5:1 and in the most preferred form in the ratio of 400 mg/20 mg. The last form is reserved for episodes of severe acute coronary insufficiency and/or severe arrhythmias.

A tablet may be made of for example, amiodarone, acebutolol, isosorbide dinitrate, or amiodarone, atenolol and isosorbide dinitrate using as excipients: lactose, maize, starch, povidone excipient, magnesium stearate, mannitol, sodium carboxy methyl cellulose, sodium carboxy methyl starch, colloidal silica.

c) Intravenous administration

The intravenous mode of administration is the preferred form of administration of the novel combinations during severe coronary insufficiency particularly in the setting of an infarction as it is the form most suitably adapted for the patient's conditions; it can be modulated with regards to the clinical evolution and the individual's susceptibility. This mode comprises the simultaneous administration of two or three compounds and the most preferred combination is that which allows the administration of three of the compounds.

Where two active substances are administered, e.g., amiodarone and nitrate in solution, a ratio varying from 100 to 1 to 5:1 and in preference in a ratio of 25:2 for bolus doses and 7:1 for maintenance doses, is used where a beta blocker is additionally employed, the amiodarone: beta blocker ratio varies from 25:1 to 25:4 for propanolol from 50:1 to 50:10 for atenolol, from 25:2 to 25:10 for acebutolol and from 25:2 to 25:15 for metoprolol.

During the first hours of acute coronary insufficiency parenteral administration of 2-6 mg/kg of amiodarone and a hourly dose of 2.5-7.5 mg/hr of ISDN are desirable. A 12 hour treatment period is suitable. The amount of amiodarone and ISDN required for optimal limitation and eventual prevention of an infarct is an average of 400 mg and 50 mg respectively administered in 12 hours for a 70 kg patient. The doses should then be adapted to clinical evolution particularly in ratios with respect to weight (approximate to exact) of amiodarone/ISDN varying from 20:1 to 5:1 preferentially 7:1 and in a way particularly preferred that contains 700 mg:100 mg to be administered within 24 hours.

The bolus doses best adapted to the setting of an acute coronary emergency comprise, in the light of experiments performed the 2 substances in the ideal ratios of 25:1 to 25:2 and in the most preferred ratio of 25:2. The necessary dose is lower in patients with a normal arterial pressure, normal systemic arterial resistance, normal pulmonary wedge pressure than in those with an elevated pulmonary capillary pressure, elevated arterial pressure or elevated systemic arteriolar resistance. Likewise, the effective and necessary doses are less important in cases of inferior infarction than in those with an anterior infarction, in long standing ischemic heart disease and in elderly patients than in coronary disease of recent onset or in young patients.

Moreover in the presence of an acute coronary insufficiency and to prevent the recurrence of a coronary insufficiency and to obtain an optimal limitation of infarct size and eventual prevention of an infrct, it is discovered that more prolonged administration is desirable. Depending on the intensity of the infarctoid syndrome or of the unstable angina it is discovered that IV administration may optimally be prolonged to 12 hours using the doses of 400 mg Amiodarone and 50 mg ISDN or to 24 hours using a total dose of 700 mg and 100 mg respectively.

Where the administration additionally requires a beta blocker, the preferred ratio of amiodarone to beta-blocker in I.V. presentation is 25:1 in case of propanolol or 25:2 in case of atenolol.

The ideal forms of the apparatus for administration of the novel combinations for acute emergencies consist therefore of (1) either a syringe comprising 2 or 3 compartments containing the 2 or 3 active substances ready for use or (2) a kit containing two or three syringes ready to be fixed to a regulator with 3 or 4 tracks whereby one is fixed to a needle ready for use and the other two or three to syringes containing the active substances already dosed according to the ratio amiodarone/ISDN varying from 25:1 to 100:1 for immediate initial injection during the first minutes of medical intervention, and in a ratio of approximately 100 mg:4 mg. for repeated injections during the early hours of infarction syndromes. The composition may comprise a beta-blocker, e.g. atenolol in an already measured quamity of 2-10 mg in one compartment.

The combination may comprise a beta-blocker other than atenolol, acebutolol, satolol and metoprolol, such as tertatolol and labetolol.

The preferred approximate dose of IV beta-blocker to replace 2 mg of Atenolol is propanolol 1 mg, metoprolol 8 mg (slow injection) acebutolol 5 mg.

The preferred dose of beta-blocker that may replace 50 mg atenolol in the combination is as follows: acebutolol approximately 100 mg of immediate release and 250 mg of slow release preparation metoprolol approximately 100 mg tertatolol approximately 2.5 mg.

The combinations hereof can consist of a nitrate derivative other than ISDN, or nitroglycerin which has been used by the inventor in this combination. The combinations consisting of trinitrine having been investigated are similar to those described above by substituting 2.5 to 7.5 mg/hr of ISDN by 15 to 300 mg/mins of nitroglycerine by intravenous means. By oral means, the combination is similar to that using ISDN by replacing 20 mg ISDN by 5 to 7.5 mg of nitroglycerine. Isosorbide mononitrate erithrityl tetanitrate and pentarerithrityl tetanitrate may also be used in the approximate or exact doses of 10-20 mg, 2-10 mg and 40-100 mg respectively in lieu of ISDN 20 mg.

The preferred achieved form of the invention in the treatment of extremely severe coronary insufficiency where human lives are at risk is that of liquid preparations suitable for parenteral administration.

EXAMPLES

EXAMPLE I

I.V. pharmaceutical preparation

Presentation: injectable solution in boxes of vials of 3 ml each.
  Hospital or Mobile Coronary Care Unit
  Presentation: Boxes of 20 vials.
  Preparation of solution so as to contain:
  isosobide dinitrate: 2 mg
  amiodarone: 25 mg
  propanolol: 1 mg
  mannitol: 3 mg
  glycine: 17.5 mg
  sodium chloride: 30 mg
  acetic acid: 0.12 mg
  water/sodium hydroxide: q.s. 3 ml at pH 7

EXAMPLE II

Another I.V. Preparation

Presentation as in Ex. I in vials. Preparation of solution so as to contain:
  isosorbide dinitrate: 2 mg
  amiodarone: 25 mg
  atenolol: 2 mg
  mannitol: 3 mg
  glycine: 17.5 mg
  sodium chloride: 30 mg
  acetic acid: 0.12 mg
  water/sodium hydroxide: q.s. 3 ml at pH 7.

EXAMPLE III

Tablet composition

A tablet is made of the three following substances and proportions:
  amiodarone, 150 mg;
  atenolol, 50 mg;
  isosorbide dinitrate, 20 mg.
Other constituents: Excipients:
  lactose: 275 mg
  maize starch: 80 mg
  povidone excipient: 6 mg
  magnesium stearate: 11 mg
  colloidal silica: 2.5 mg.

EXAMPLE IV

A capsule containing two or three compartments (i) A capsule is made of 3 compartments so as to comprise the following active substances and inactive ingredients, 1 compartment to comprise Isosorbide mononitrate and its associated inactive ingredients for prolonged release.

| Active Substances (approximate composition) | Inactive Ingredients (approximate composition) (in gm) | |
| --- | --- | --- |
| 1. Amiodarone chlorhydrate 0.075 g | Lactose | 0.025 |
| | Maize starch | |
| | Polyvidone excipient | 0.002 |
| | Anhydrous colloidal silica | 0.0009 |
| | Magnesium stearate | 0.0017 |
| | Purified Water | 0.022 |
| 2. Acebutolol chlorhydrate 0.200 g | Lactose | 0.15 |
| | Maize Starch | 0.45 |
| | Polyvidone | 0.013 |
| | Magnesium stearate | 0.004 |
| | Talc | 0.001 |
| | Aerosil 200 | 0.001 |
| 3. Isosorbide 5' mononitrate 0.030 g | Lactose | 0.090 g |
| | Microgranules of saccharose & maize starch: | |
| | Saccharose | 0.033 g |
| | Maize starch | 0.011 g |
| | Polymer of metacrylic acid and of esters of methacrylic acid | |
| | (Eudragit L) | 0.006 g |
| | Gum | 0.090 g |

(ii) A capsule containing two compartments:
First compartment: amiodarone 100 mg with inactive ingredients as in (i) above and either nitroglycerin 5 mg or Isosorbide dinitrate 10 mg and
  Talc: 0,009
  lactose: 275 mg
  maize starch: 80 mg
  povidone excipient: 6 mg
  magnesium stearate: 11 mg
  colloidal silica: 2.5 mg.
Second Compartment: acebutolol in prolonged release form.

EXAMPLE V

A tablet for both sub-lingual and gastro-intestinal administration

Isosorbide dinitrate
for immediate sub-lingual release: 2.5 mg
for gastro-intestinal release: 15 mg
amiodarone: 150 mg
metoprolol: 50 mg.
Excipients:
lactose: 300 mg
maize starch: 100 mg
povidone excipient: 6 mg
magnesium stearate: 15 mg
colloidal silica: 2.5 mg.

EXAMPLE VI

Preparation for oral administration in emergency isosorbide dinitrate: 5 mg for sub-lingual release
isosorbide dinitrate: 15 mg for gastro-intestinal release after oral absorption.
amiodarone: 400 mg
atenolol: 50 mg.
Excipients:
lactose: 300 mg
maize starch: 100 mg
povidone excipient: 6 mg
magnesium stearate: 15 mg
colloidal silica: 2.5 mg.

In Examples III through VI instead of atenolol, the combination may consist of another beta-blocker namely acebutolol, metoprolol, sotalol, tertatolol and propanolol. A dose of 100 mg acebutolol of classical release pattern or 250 mg of slow release pattern may replace 50 mg atenolol in the preparation and a dose of 100 mg of metroprolol or 40 mg of sotalol, or 2.5 mg of tertatolol or 20 mg of propanolol may also replace 50 mg of atenolol in the oral preparation.

EXAMPLE VII

Prepared syringes and kits and methods of treatment of emergencies

Because of the necessity to adapt doses to individual cases and with the aim of preventing sudden deaths, a device is utilized that comprises in one unit:

(i) An already prepared syringe containing in one compartment a dose of 25 mg of amiodarone for bolus injection, in another compartment a dose of 100 mg of amiodarone for administration in a delay varying from 2 to 5 minutes after the first injection and a compartment containing 200 mg of amiodarone to be administered within a delay of 15 to 60 minutes after the second injection.

(ii) A compartment of a syringe containing 2 mg ISDN, another compartment containing 4 mg ISDN.

EXAMPLE VIII

Pre-filled syringes containing the compositions hereof

Mode (i) A prefilled multi-barrelled syringe containing in separate compartments for simultaneous administration:

(a)

isosorbide dinitrate: 2 mg
water: 2 ml
acetic acid: 0.12 mg
glycine: 17.5 mg
mannitol: 3 mg.

(b)

amiodarone: 25 mg.
benzyl alcohol: 15 mg
polysorbate 80: 50 mg
water: 0.5 ml.

(c)

propanolol: 1 mg
citric acid: 20 mg
water: 1 ml.

Mode (ii) A prefilled syringe containing in separate compartments (a)

isosorbide dinitrate: 8 mg
water: 8 ml
acetic acid: 0.48 mg
glycine: 70 mg
mannitol: 12 mg.

(b)

amiodarone: 100 mg
benzyl alcohol: 60 mg
polysorbate 80: 200 mg
water: 2 ml.

(c)

atenolol: 8 mg
citric acid: 20 mg
water 1 ml.

The syringe may be activated by a programmable micropump so as to eject individually adjusted doses of the preparation.

EXAMPLE IX

Kit for management of acute coronary insufficiency

A device or kit to comprise the syringe described in Example VIII Mode (i) and in lieu of IV ISDN described in Example VIII Mode (ii) above, a packet of nitroglycerin and/or ISDN 5 mg for sublingual administration and/or an inhaler of a nitrate derivative example ISDN (dose of 1.5 mg) or nitroglycerin or isosorbide mononitrate.

Availability of this kit will allow the physician to start immediately the appropriate management to prevent sudden death and to limit the size of the infarction.

EXAMPLE X

Alternative dosage equivalents

It will be understood by those skilled in the art that the different nitrates and beta blockers utilized in the present invention have different strengths per unit weight. Thus for a given range of dosage amount of amiodarone the equivalents of the other coagents which may be utilized in the compositions and methods of the present invention are set forth below:

| Nitrate | Oral Dose | Bolus | Maintenance |
|---|---|---|---|
| Isosorbide Dinitrate | 10-20 mg | 2-10 mg | 2-50 mg |
| Nitroglycerine | 2.5-10 mg | 0.1-2 mg | 15-150 ug/mn = 0.9-9 mg |
| Pentaerythrityl Tetranitrate | 10-100 mg | | |

-continued

| Nitrate | Oral Dose | Bolus | Maintenance |
|---|---|---|---|
| Isosorbide mononitrate | 5-40 mg | | |
| Erithrityl Tetranitrate | 5-10 mg | | |
| Beta Blockers | | | |
| Propanolol | 20-80 mg | 1-5 mg | |
| Sotalol | 40-80 mg | 2-40 mg | |
| Acebutolol | 100-500 mg | 5-25 mg | |
| Atenolol | 25-100 mg | 1-5 mg | |
| Metoprolol | 25-100 mg | 1-5 mg | |
| Pindolol | 5-10 mg | | |
| Tertalol | 2.5-5 mg | | |
| Amiodarone | 50-400 mg | 25-100 mg | 0.5-20 mg/kg/day |

EXAMPLE XI

A Method of Treatment of Chronic Coronary Insufficiency with a View to Improve the Quality of Life and to Prevent the Recurrence of Sudden Death The sensitivity to a beta-blocker should first be determined by a test dose of a beta-blocker for example atenolol 50 mg administered orally on the first day and atenolol 100 mg to be administered on the second day. The absence of any unusually intense bradycardia, hypotension or atrio-ventricular block after the beta-blocker allows the use the invented preparations containing the 3 active substances.

One of the preparations of the present invention e.g. Example III is administered twice daily for six to 10 days until an optimal decrease in heart rate is observed e.g. so as to achieve a resting heart rate between 60 and 70.

The dose is then adapted to the results obtained and will usually vary between ½ and 11/2 tablet per day.

EXAMPLE XII

Examples of a method of treatment of the acute coronary insufficiency present in the myocardial syndrome and in unstable angina with a view to prevent the occurrence of a myocardial infarction, to limit its size and to prevent sudden deaths Oral administration of the preparation in Example VI by the patient prior to the arrival of the medical team and as soon as possible after onset of chest pain.

Administration by the physician or CPR team of the preparation of Example I intrvenously. Repeated bolus injections to be administered by the medical team according to observed results on blood pressure, heart rate and other clinical symptoms and signs. This is followed by a continuous infusion of a preparation containing the 2 or 3 active substances.

I claim:

1. A method of providing cardioprotective action to a patient suffering from coronary insufficiency and complications thereof which comprises administering to such patient a cardioprotectively sufficient amount of protective agents comprising at least one member of the group consisting of
   A i) amiodarone in conjunction with
   ii) at least one coronary vasodilator having at least one nitro group selected from the group consisting of isosorbide mononitrate, isosorbide dinitrate, pentaerythrityl tetranitrate, erythrityl tetranitrate and nitroglycerine, and
   B ii) a beta blocker selected from the group consisting of acetbutolol, metoprolol, propranolol and atenolol.

2. A method of claim 1 wherein the amiodarone is administered in conjunction with at least one said vaso dilator and at least one said beta blocker.

3. A method of claim 1 wherein the protective agents are administered separately.

4. A method of claim 1 wherein the protective agents are administered in associated form.

5. A method of claim 1 wherein the ratio by weight of amidarone to the nitro containing coronary dilator to beta blocker is 100 to between 1 and 100 to between 4 and 500.

6. A method of claim 1 wherein the administered dosage is between about 0.3 and about 30 kg body weight per day.

7. A method of claim 1 wherein the protective agents are administered within the first 30 minutes after onset of apparent cardiac insufficiency.

8. A method of claim 1 wherein the administration is repeated at least once at intervals of between 30 and 60 minutes after the first administration.

9. A method of claim 1 wherein the nitro containing dilator is selected from the group consisting to trinitrine and is isosorbide dinitrate and the beta blocker is selected from the group consisting of acetbutolol, metoprolol and atenolol.

10. A cardioprotective agent for administration to a patient suffering from coronary insufficiency to thereby reduce the probability of incidence of myocardial infarction in such a patient which comprises a combination selected from the group consisting of
    A i) cardioprotectively sufficient amounts of amiodarone, in the presence of
    ii) at least one coronary vasodilator having at least one nitro group selected from the group consisting of isosorbide mononitrate, isosorbide dinitrate, pentaerythrityl tetranitrate, erythrityl tetranitrate and nitroglycerine, and
    B iii) a beta blocker selected from the group consisting of acetbutolol, metoprolol, propranolol and atenolol, in the presence of
    C iv) a pharmacologically acceptable carrier.

11. An agent of claim 10 wherein the amiodarone is combined with at least one said vaso dilator and at least one said beta blocker.

12. An agent of claim 10 wherein the ratio by weight of amidarone to the nitro containing coronary dilator to beta blocker is 100 to between 1 and 100 to between 4 and 50.

13. An agent of claim 12 wherein the nitro containing dilator is selected from the group consisting to nitroglycerine, isosorbide mononitrate and isosorbide dinitrate and the beta blocker is selected from the group consisting of propanolol, acebutolol, metoprolol and atenolol.

14. An agent of claim 12 wherein the components are compounded in a form suitable for administration by the oral, sublingual, intravenous, subcutaneous, or inhalation administrative routes.

15. A method of providing cardioprotective action to a patient suffering from coronary insufficiency and complications thereof which comprises administering to such patient a cardioprotectively sufficient amount of protective agents comprising
    A i) amiodarone in conjunction with ii) at least one coronary vasodilator having at least one nitro group selected from the group consisting of isosorbide mononitrate. isosorbide dinitrate. pentaerythrityl tetranitrate. erythrityl tetranitrate and nitroglycerine, and iii) a beta blocker selected from the group consisting of acetbutolol. metoprolol. propranolol and atenolol.

16. A method of claim 15 wherein the amiodarone is administered in conjunction with one said vaso dilator and one said beta blocker.

17. A cardioprotective agent for administration to a patient suffering from coronary insufficiency to thereby reduce the probability of incidence of myocardial infraction in such a patient which comprises a combination of A i) cardioprotectively sufficient amounts of amiodarone, in the presence of ii) at least one coronary vasodilator having at least one nitro group selected from the group consisting of isosorbide mononitrate. isosorbide dinitrate. pentaerythrityl tetranitrate. erythrityl tetranitrate and nitroglycerine, and B ii) a beta blocker selected from the group consisting of acetbutolol, metoprolol, propranolol and atenolol, in the presence of C iv) a pharmacologically acceptable carrier.

18. An agent of claim 17 wherein the amiodarone is combined with one said vasodilator and one said beta blocker.

* * * * *